United States Patent [19]

Fukushima et al.

[11] Patent Number: 4,560,703
[45] Date of Patent: Dec. 24, 1985

[54] CLAVULONE DERIVATIVES, PROCESS FOR PREPARING THE SAME, AND USE OF SAID COMPOUNDS

[75] Inventors: Masanori Fukushima, Nagoya; Osamu Hirai, Toyonaka; Toshitaka Manda, Osaka; Hiroyuki Kikuchi, Nishinomiya; Yasumasa Tsukitani, Sakuramura; Iwao Shimizu, Toyonaka; Yasuji Yamada, Hachioji, all of Japan

[73] Assignee: Fujisawa Pharmaceutical Co., Ltd., Osaka, Japan

[21] Appl. No.: 535,258

[22] Filed: Sep. 23, 1983

[30] Foreign Application Priority Data

Sep. 27, 1982 [JP] Japan ............................ 57-169148
Apr. 2, 1983 [JP] Japan ............................ 58-58547
Jun. 22, 1983 [JP] Japan ............................ 58-112378

[51] Int. Cl.⁴ ............... C07C 69/732; C07C 69/738; A61K 31/215
[52] U.S. Cl. ................................. 514/530; 560/121
[58] Field of Search ............ 560/121; 562/503; 424/305; 514/530

[56] References Cited

PUBLICATIONS

Iguchi et al., Tet. Letters, 24(41) 4433 (1983).
K. Kuchi et al., Tet. Letters 23(49) 5171 (1982).
Kobayashi et al., Tet. Letters 23(50) 5331 (1982).

*Primary Examiner*—Robert Gerstl
*Attorney, Agent, or Firm*—Oblon, Fisher, Spivak, McClelland & Maier

[57] ABSTRACT

Novel clavulone derivatives of the formula:

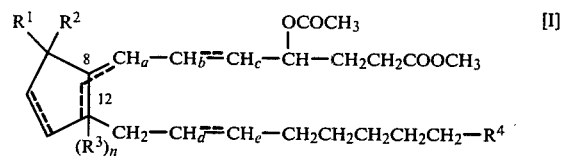

wherein $R^1$ and $R^2$ combine together to form a keto group or either one of $R^1$ and $R^2$ is hydrogen atom and another one of them is hydroxy or acetoxy group, $R^3$ and $R^4$ are the same or different and are each hydrogen atom or acetoxy group, n is 0 or 1, provided that when the C—C bond between 8 and 12 positions is double bond, n is 0, a, b, c, d and e are each an integer of 1 or 2, and the dotted line means that the C—C bond is a single bond or double bond, or a salt thereof, which have excellent anti-inflammatory activity and anti-tumor activity and hence are useful as an anti-inflammatory agent or anti-tumor agent.

15 Claims, No Drawings

CLAVULONE DERIVATIVES, PROCESS FOR PREPARING THE SAME, AND USE OF SAID COMPOUNDS

BACKGROUND OF THE INVENTION

1. Field of the Invention

The present invention relates to novel clavulone derivatives, a process for preparing the same, and use of said clavulone derivatives as a medicine. More particularly, it relates to clavulone derivatives of the formula:

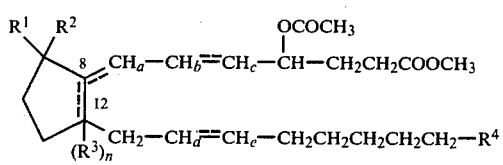

wherein $R^1$ and $R^2$ combine together to form a keto group or either one of $R^1$ and $R^2$ is hydrogen atom and another one of them is hydroxy or acetoxy group, $R^3$ and $R^4$ are the same or different and are each hydrogen atom or acetoxy group, n is 0 or 1, provided that when the C—C bond between 8 and 12 positions is double bond, n is 0, a, b, c, d and e are each an integer of 1 or 2, and the dotted line means that the C—C bond is a single bond or double bond, or a salt thereof, and a process for preparing the clavulone derivatives, and use thereof as a medicine, particularly as an anti-inflammatory or an anti-tumor agent.

2. Description of the Invention

Some of the clavulone derivatives [I] are extracted from the soft coral *Clavularia viridis* and others are chemically derived from the extracted compounds. These clavulone derivatives [I] of the present invention have some pharmacological activities such as anti-inflammatory and anti-tumor activities and are useful as a medicine.

The clavulone derivatives [I] include one or more stereoisomers such as optical and/or geometrical isomers due to asymmetric carbon atom(s) and double bond(s) in those molecules, and these isomers are also included within the scope of the present invention.

The clavulone derivatives [I] include specifically the compounds of the following formulae and their salts.

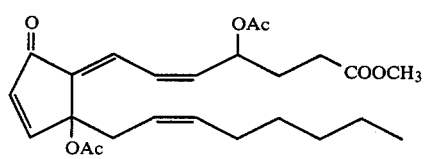
(1)

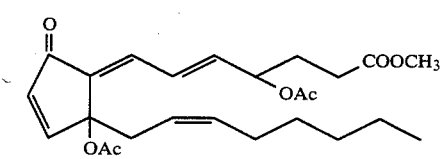
(2)

-continued

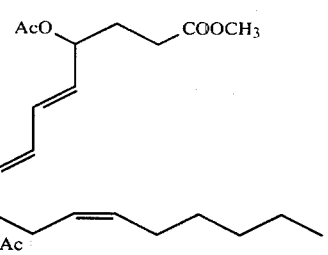
(3)

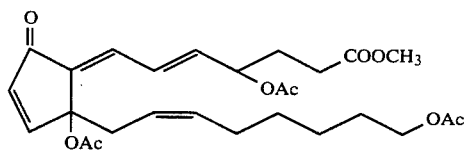
(4)

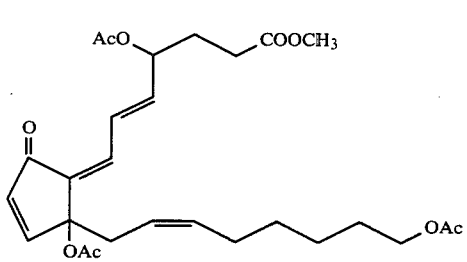
(5)

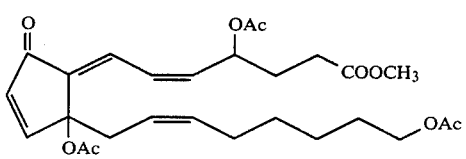
(6)

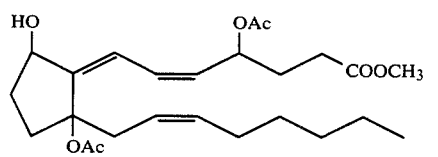
(7)

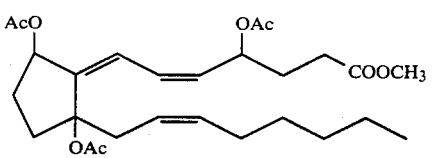
(8)

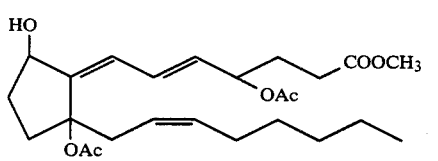
(9)

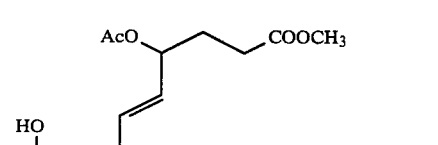
(10)

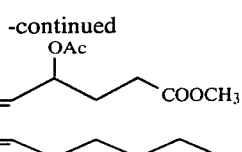

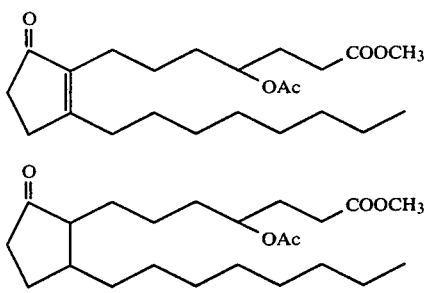

in the above formulae, Ac means acetyl group.

The compounds of the above formulae (1) to (13) are designated "clavulone-1" to "clavulone-13", respectively. The salts of the clavulone derivatives (I) include conventional pharmaceutically acceptable salts such as salts of alkali metals (e.g. sodium, potassium), salts of alkaline earth metals (e.g. magnesium, calcium), salts of amino acids (e.g. glutamic acid), or the like.

Among clavulone-1 to clavulone-13, clavulone-1 to clavulone-6 are isolated from the soft coral *Clavularia viridis* by the steps of extracting roughly the soft coral with methanol, concentrating the crude extract, extracting the concentrated solution with ethyl acetate after dissolving it in water, subjecting the extract to silica gel chromatography, eluting with a mixed solvent of benzene-ethyl acetate (10:1 by volume), separating three fractions containing clavulone-1 to clavulone-3 under detecting with thin layer chromatography (TLC, Kiesel gel 60, solvent, benzene-ethyl acetate=4:1 by volume), and further separating other fractions by changing the solvent to benzene-ethyl acetate=5:1 by volume under detecting with thin layer chromatography, from which clavulone-4 to clavulone-6 being isolated.

Clavulone-7 to clavulone-13 are chemically derived from the above clavulone derivatives isolated from the soft coral. That is, when clavulone-1, clavulone-2 and clavulone-3 are reduced with a borohydride catalyst such as sodium borohydride or lithium borohydride in a usual manner to give the corresponding compounds wherein the double bond in the cyclopentane nucleus is saturated and the keto group at 9-position is reduced into hydroxy groups, i.e. clavulone-7, clavulone-9 and clavulone-10, respectively. Treatment of the compounds obtained by the above reduction with a conventional acetylating agent such as acetic anhydride or an acetyl halide gives the corresponding compounds wherein the hydroxy group at 9-position is acetylated. For example, when clavulone-7 is treated with acetic anhydride in a usual manner, clavulone-8 is obtained. Besides, oxidation of the compounds obtained by the above reduction treatment with an appropriate oxidizing agent such as pyridinium chlorochromate gives the corresponding compounds wherein the hydroxy group at 9-position is converted into a keto group. For example, when clavulone-7 is treated with pyridinium chlorochromate, clavulone-11 is obtained. Moreover, when clavulone-1, clavulone-2 and clavulone-3 are reduced by a conventional catalytic reduction, for example, by hydrogenating in the presence of a catalyst such as palladium-carbon, there are obtained the corresponding compounds wherein the double bond is wholly or partially saturated, i.e. clavulone-12 and clavulone-13 from all of the clavulone-1 to clavulone-3.

The clavulone deivatives (I) of the present invention have excellent pharmacological activities such as anti-inflammatory and anti-tumor activities. The pharmacological activities of the clavulone derivatives are shown by the following experiments.

(1) Experiment 1: Anti-inflammatory activity

The anti-inflammatory activity was tested by the inhibitory effect on proliferation of granulation tissue which is one of the tests for determining anti-inflammatory activity as follows:

Method (fertile egg method)

Fertile eggs of Babcock strain chickens were incubated at 38° C. for 9 days. The shell and shell membrane were then removed according to the method of D'arcy et al (cf. D'arcy, P. F. et al, *Brit. J. Pharmac. Chemother.*, 29, 378 (1967). A sterile filter paper disc (diameter: 9 mm) was implanted on the chorio-allantoic membrane and the opening in the shell was sealed with cellophane tape. The eggs were then reincubated for 4 days and at the end of this period, the filter paper disc with granulation tissue was dissected from the chorio-allantoic membrane and then dried at 60° C. for 12 hours. In order to assess the actual amount of granulation tissue present, the weight of filter paper disc which was used in this experiment was subtracted from the total weight of the disc plus granulation tissue.

The test compound was dissolved in an organic solvent (acetone) and 20 $\mu$l of the solution was applied on the each disc. The disc was dried and then used in this test. The mean weight of the granulation tissue in each group was compared with that of the control group which was treated with a vehicle alone.

Results

Clavulone-1, clavulone-2, clavulone-3, clavulone-4 and clavulone-5 were used as the test compounds. As the result, these compounds showed the inhibitory effect on proliferation of granulation tissue as shown in the following Table 1.

TABLE 1

| Test compounds | Dose (g) | Inhibitory rate (%) |
|---|---|---|
| Clavulone-1 | 30 | 15.8 |
| | 100 | 30.4 |
| Clavulone-2 | 30 | 10.1 |
| | 100 | 21.0 |
| Clavulone-3 | 30 | 26.1 |
| | 100 | 31.0 |
| Clavulone-4 | 30 | 18.3 |
| | 100 | 34.2 |
| Clavulone-5 | 30 | 18.2 |
| | 100 | 31.6 |

Moreover, the anti-tumor activities of the clavulone derivatives (I) were tested by the inhibitory activity on propagation of leukemia L-1210 cells, DBA/MC fibrosarcoma cells, and B-16 melanoma cells in mice and also apothanasia effect of mice implanted with leukemia P388 cells and Ehrlich carcinoma cells as in the following experiments.

(2) Experiment 2: Inhibitory activity on proliferation of leukemia L-1210 cells

Preparation of drug

The test compounds (clavulone-1, -2 and -3) were each dissolved in ethanol and diluted with a medium (RPMI-1640) in a prescribed concentration. Said RPMI-1640 medium contained 10% by weight of fetal calf serum.

Cell culture

Leukemia L-1210 cells (cell concentration: $1 \times 10^5$ cells/ml) were inoculated in the RPMI-1640 medium containing the test compound (0.1 to 4.0 μg/ml) and cultured under the conditions of 5% $CO_2$ in air, saturated humidity and at 37° C. for 4 days.

DETERMINATION OF THE INHIBITORY ACTIVITY

Immediately after the cultivation, the L-1210 cells were stained with trypan blue. Number of viable cells (i.e. cells which were not stained with trypan blue) was counted, and the number of viable cells was compared with that in the control group (no drug was added). The results are shown in Table 2, wherein the number of viable cells in the control group was counted as 100.

TABLE 2

| | Growth Rate (%): | | | | |
|---|---|---|---|---|---|
| | Concentration of test compounds (μg/ml) | | | | |
| | 0 | 0.1 | 0.2 | 0.4 | 1.0 |
| Clavulone-1 | 100 | 100 | — | 24.7 | 0 |
| Clavulone-2 | 100 | 61.5 | 55.4 | 16.9 | 0 |
| Clavulone-3 | 100 | 87.5 | 52.0 | 17.2 | 0 |

(3) Experiment 3: Inhibitory activity on proliferation of DBA/MC fibrosarcoma cells Preparation of drug The test compounds (clavulone derivatives) were each dissolved in ethanol and diluted with a phosphate-buffer physiological saline solution and further diluted with an eagle's MEM medium in a prescribed concentration. Said eagle's MEM medium contained 20% by weight of fetal calf serum and 0.4% by weight of lactalubumin hydrolysates.

Cell culture

DBA/MC Fibrosarcoma cells (cell concentration: $2.5 \times 10^4$ cells/ml) were floated on the eagle's MEM medium and cultured under the conditions of 5% $CO_2$ in air, saturated humidity and at 37° C. for 24 hours. Thereafter, the medium was replaced with the above test compound-containing medium and then it was cultured under the same conditions for 48 hours.

Determination of the inhibitory activity

Immediately after the cultivation, the DBA/MC cells were fised with methanol and stained with Giemsa solution. The stained cells were counted with a microscope, and the number of stained cells was compared with that of the control group (no test compound was added). The inhibitory rate was calculated by the following equation:

$$\text{Inhibitory rate (\%)} = \left(1 - \frac{\text{Number of stained cells in test group}}{\text{Number of stained cells in the control group}}\right) \times 100$$

The results are shown in the following Table 3.

TABLE 3

| | Inhibitory Rate (%): | | |
|---|---|---|---|
| | Concentration of test compound (μg/ml) | | |
| | 3.0 | 20.0 | 30.0 |
| Clavulone-1 | 50 | 100 | — |
| Clavulone-2 | 0 | 100 | — |
| Clavulone-3 | 0 | 100 | — |
| Clavulone-4 | 0 | 100 | — |
| Clavulone-5 | 0 | 100 | — |
| Clavulone-6 | 90 | 100 | 100 |
| Clavulone-13 | 0 | — | 100 |

(4) Experiment 4: Apothanasia effect in mice implanted with leukemia P388 cells

Preparation of drug

Clavulone-2 was mixed with gum arabic in the ratio of 1.6:1 by weight and was mixed with a physiological saline solution in a prescribed concentration to give a test compound solution.

Method

BDFI male mice (5 weeks old, weighing 22.0-24.4 g, 6 animals per group) were used.

Each mice was inoculated intraperitoneally with leukemia P388 cells (cell concentration: $1 \times 10^7$ cells/ml) in 0.2 ml Hank's solution. A solution of a test compound in a physiological saline solution was injected intraperitoneally once a day from the first day to 4th day and also from 7th day to 11th day after inoculation of the tumor cells. The control group was given with a vehicle (a physiological saline solution) alone in the same way.

Evaluation of effects

After inoculation of the tumor cells, the survivors were observed for two weeks. The apothanasia effect of the test compound was estimated by comparing mean survival time between the medicated group and the control group by the following equation:

$$\text{Apothanasia effect (\%)} = \frac{\text{Mean survival time of the medicated group}}{\text{Mean survival time of the control group}} \times 100$$

The results are shown in the following Table 4.

TABLE 4

| | Apothanasia effect (%) | |
|---|---|---|
| | Dose (mg/kg) | |
| | 4.0 | 8.0 |
| Clavulone-2 | 130 | 130 |

(5) Experiment 5

Materials and method

Animals:

Six or twelve female ICR strain mice (6 weeks old, weighing 22.2–26.8 g) were used.

Preparation of test drug:

The test drug was prepared by mixing clavulone-2 with gum arabic, suspending the mixture in a sterilized saline solution in a concentration of clavulone-2 of 10, 18 or 25 mg/10 ml.

Tumor cells:

Ehrlich carcinoma cells were serially passaged in an ascites form in ICR strain mice. The tumor cells were harvested from ICR strain mice on 6th day after inoculation, washed with and resuspended in Hank's solution in a concentration of $5 \times 10^5$ cells/ml.

Inoculation of tumor cells and injection of test drug:

Tumor cells ($1 \times 10^5$ cells/0.2 ml/mouse) were implanted intraperitoneally. The test drug (clavulone-2, 10 ml/kg) was injected intraperitoneally once a day from first to 4th day after the implantation of tumor cells. Control mice were injected with a saline solution in the same as above.

Evaluation of anti-tumor effect of clavulone-2:

After the implantation of tumor cells, each mouse was observed for 60 days. The anti-tumor effect of clavulone-2 was evaluated by means of I.L.S. (%) which was calculated by the following equation:

$$I.L.S. (\%) = \left( \frac{MST \text{ in medicated group}}{MST \text{ in control group}} - 1 \right) \times 100$$

[Note]:
MST is median survival time.
I.L.S. is increase of life span.

When the value of 25 or more I.L.S. is obtained, the test compound was evaluated as it was effective.

Results

The results are shown in Table 5. As is shown in the table, clavulone-2 showed high activity against Ehrlich ascites tumor in vivo, and surprisingly, 50% of animals in the group treated with clavulone-2 in an amount of 18 mg/10 ml/kg were survived even 60 days after implantation of tumor cells.

TABLE 5

| Dose of clavulone-2 (mg/kg) | MST (Day) | I.L.S. (%) | Survivors on 60th day/number of mice in one group |
|---|---|---|---|
| 0 | 21.5 | — | 0/12 |
| 10 | 26.5 | 23 | 2/6 |
| 18 | 50.0 | 133 | 3/6 |

(6) Experiment 6

Materials and method

Animals:

C57BL/6 female mice (12 weeks old, weighing 18.4–21.6 g, each group: 10 animals) were used.

Preparation of test drug:

The test drug was prepared by dissolving clavulone-2 in ethanol and diluting with a saline solution in a concentration of clavulone-2 of 100 μg/ml.

Tumor cells:

B-16 melanoma cells were serially passaged in subcutaneously implanted form in C57BL/6 mice. The tumor cells were dissected out from C57BL/6 mice on 16th day after implantation, weighed, and mixed homogeneously with Hank's solution in a ratio of 1:9 by weight.

Inoculation of tumor cells and injection of test drug:

Tumor cells ($2 \times 10^5$ cells/0.05 ml/mouse) were implanted subcutaneously. The test drug (clavulone-2, 10 μg/0.1 ml) was injected locally into tumor cell-implanted site for three weeks except the weekend. Control mice were injected with a vehicle (1% ethanol in saline solution) in the same as above.

Evaluation of anti-tumor effect of clavulone-2:

After 21 days from the implantation of tumor cells, mice were killed by chloroform anethesia, and the tumor masses were removed and weighed. The anti-tumor effect of clavulone-2 was evaluated by means of growth inhibition rate calculated by the following equation:

$$\text{Growth inhibition rate } (\%) = (1 - T/C) \times 100$$

T: Mean tumor weight of mice treated with the test compound-containing solution
C: Mean tumor weight of mice treated with the vehicle solution.

Results

The results are shown in the following Table 6. As is shown in the table, clavulone-6 regressed significantly the growth of B-16 melamona in mice, and the growth inhibition rate was 73%.

TABLE 6

| Dose (μg/0.1 ml) | Mean tumor weight (g; ± S.E.) | Growth inhibition rate (%) |
|---|---|---|
| 0 | 3.298 ± 0.155 (6)* | — |
| 10 | 0.882 ± 0.388 (10) | 73 |

(Note): *Number in parentheses indicates the number of survivors 21th day after implantation of tumor cells. S.E. is standard error.

As is clear from the above experimental results, the clavulone derivatives (I) of the present invention are excellent anti-inflammatory and anti-tumor activities and are useful as an anti-inflammatory agent and anti-tumor agent in human and other animals.

The clavulone derivatives (I) and their salts of the present invention are used in conventional pharmaceutically acceptable preparations suitable for using as a medicine, such as powders, granules, tablets, capsules, microcapsules, suppositories, suspensions, solutions, emulsions, injections, or the like.

These pharmaceutical preparations can be prepared by a conventional method by using conventional carriers or diluents, such as excipients, bulking agents, binding agents, wetting agents, disintegrators, surface active agents, lubricants, dispersing agents, buffering agents, preservatives, solubilizers, solvents, or the like.

Dose of the clavulone derivatives and their salts may optionally vary with administration routes, age and weight of patients, severity of diseases, or the like, but is usually in the range of 0.01 mg to 0.1 g per kg of body weight per day, preferably 1 mg to 0.1 mg per kg of body weight per day, which may be divided into several times.

The preparation may contain other pharmaceutically active compounds in addition to clavulone derivatives (I) or their salts.

The present invention is illustrated by the following Examples but should not be construed to be limited thereto.

EXAMPLE 1

Extraction and isolation of clavulone-1 to clavulone-6

(a) Lyophilized product of *Clavularia viridis* (5 kg) is crushed in methanol (20 liters). After allowing the crushed product to stand overnight, the mixture is filtered. The residue is extracted with methanol (20 liters) at room temperature. The extract is combined with the filtrate obtained above, and the mixture is concentrated under reduced pressure below 50° C. The concentrated extract is suspended in water (3 liters) and extracted twice with ethyl acetate (2 liters). The ethyl acetate solutions are combined and concentrated under reduced pressure to give a dark green extract (30 g).

The extract (30 g) thus obtained is subjected to silica gel column chromatography (6×40 cm, dry pack, manufactured by Merck & Co.), followed by eluting with benzene-ethyl acetate (10:1 by volume) to obtain the following fractions:

Fraction-1 (about 2 liters, weight after removing the solvent: 2.8 g),

Fraction-2 (1 liter, weight after removing the solvent: 12.4 g),

Fraction-3 (0.5 liter, weight after removing the solvent: 2.4 g),

Fraction-4 (2.5 liters, weight after removing the solvent: 3.2 g)

Thereafter, the elution is continued except that the eluting solvent is changed to benzene-ethyl acetate (5:1 by volume) under detecting by thin layer chromatography (kiesel gel 60, benzene-ethyl acetate=4:1 by volume) to obtain the following fractions:

Fraction-5 (0.86 g, weight after removal of the solvent)

Fraction-6 (1.1 g, weight after removal of the solvent)

(b) Isolation of clavulone-1

Fraction-4 (3.2 g) obtained above is passed through a polystyrene gel column in order to decolor, followed by eluting with methanol. The eluted extract thus obtained is passed through a silica gel column (4×70 cm, dry pack, manufactured by Merck & Co.) and eluted with benzene-ethyl acetate (15:1 by volume), and thereby a fraction having a chromatographically single spot is isolated under detecting by thin layer chromatography (Kiesel gel 60, manufactured by Merck & Co., benzene-ethyl acetate=5:1). The eluate is concentrated under reduced pressure to give a pale yellow, syrup-like clavulone-1 (240 mg). Other fraction (1.1 g) containing a few impurities is additionally obtained.

The compound obtained above has a molecular formula: $C_{25}H_{34}O_7$ and has a chemical structure of the formula (1) as shown hereinbefore and has the following properties.

High mass spectrum: 446.2305 (error: 0.2 mMU);
$[\alpha]_D$ (CHCl$_3$): $-28.9°$ (c=0.36);
UV$\lambda_{max}^{EtOH}$ (nm): 230 ($\epsilon$=13,600), 292 ($\epsilon$=17,300);
IR$\nu_{max}^{film}$ (cm$^{-1}$): 1730, 1700, 1635, 1230;
$^1$H-NMR (270 MHz) (CDCl$_3$, δppm): 0.88 (3H, t, J=6.7 Hz), 2.03 (3H, s), 2.05 (3H, s), 2.38 (2H, t, J=7.7 Hz), 2.66 (1H, dd, J=7, 14.5 Hz), 2.97 (1H, dd, J=7, 14.5 Hz), 3.70 (3H, s), 5.22 (1H, dt, J=10.9, 7 Hz), 5.45 (1H, dt, J=10.9, 8 Hz), 5.78 (1H, m), 5.86 (1H, t, J=10 Hz), 6.42 (1H, d, J=6.3 Hz), 6.59 (1H, dd, J=10, 12.5 Hz), 7.25 (1H, d, J=12.5 Hz), 7.47 (1H, d, J=6.3 Hz);
$^{13}$C-NMR (67.8 MHz) (CDCl$_3$, δppm): 14.0 (q), 20.9 (q), 21.2 (q), 22.5 (t), 27.4 (t), 29.0 (t), 29.8 (t), 29.8 (t), 31.4 (t), 35.9 (t), 51.7 (q), 69.4 (d), 85.2 (s), 121.0 (d), 124.3 (d), 124.4 (d), 134.9 (d), 134.9 (d), 137.5 (s), 138.7 (d), 157.8 (d), 169.0 (s), 169.7 (s), 172.7 (s), 193.0 (s).

(c) Isolation of clavulone-2: Fraction-3 (2.4 g) obtained above is passed through a polystyrene gel column (3×45 cm, Hitachi 3010) in order to decolor and eluted with methanol. The resulting eluate is treated in the same manner as described in the above (b) to obtain a fraction having a chromatographically single spot. The fraction is concentrated under reduced pressure to give a pale yellow, syrup-like clavulone-2 (530 mg). Other fraction (0.31 g) containing a few impurities is additionally obtained.

The compound obtained above has a molecular formula: $C_{25}H_{34}O_7$ and has a chemical structure of the formula (2) as shown hereinbefore and shows the following properties:

High mass spectrum: 446.2292 (error: −1.0 mMU);
$[\alpha]_D$ (CHCl$_3$): +10.9° (c=0.35);
UV$\lambda_{max}^{EtOH}$ (nm): 230 ($\epsilon$=14,500), 292 ($\epsilon$=19,300);
IR$\nu_{max}^{film}$ cm$^{-1}$): 1730, 1700, 1640, 1230;
$^1$H-NMR (270 MHz) (CDCl$_3$, δppm): 0.88 (3H, t, J=6.9 Hz), 2.07 (3H, s), 2.08 (3H, s), 2.38 (2H, t, J=7.5 Hz), 2.69 (1H, dd, J=8, 14.5 Hz), 2.88 (1H, dd, J=7, 14.5 Hz), 3.68 (3H, s), 5.22 (1H, m), 5.52 (1H, dt, J=10.9, 8 Hz), 5.42 (1H, q, J=7 Hz), 6.02 (1H, dd, J=7, 14.5 Hz), 6.41 (1H, d, J=6.3 Hz), 6.75 (1H, dd, J=11.6, 14.5 Hz), 6.87 (1H, d, J=11.6 Hz), 7.47 (1H, d, J=6.3 Hz);
$^{13}$C-NMR (67.8 MHz) (CDCl$_3$, δppm): 14.0 (q), 21.0 (q), 21.2 (q), 22.5 (t), 27.4 (t), 29.1 (t), 29.1 (t), 29.6 (t), 31.5 (t), 36.0 (t), 51.8 (q), 72.8 (d), 85.1 (s), 121.1 (d), 126.9 (d), 129.3 (d), 135.0 (d), 135.0 (d), 137.0 (s), 141.3 (d), 158.1 (d), 169.5 (s), 169.9 (s), 172.9 (s), 193.4 (s).

(d) Isolation of clavulone-3:

Fraction-2 (12.4 g) obtained above is passed through a polystyrene gel column (4×60 cm) in order to decolor and eluted with methanol to give pale yellow, syrup-like extract (3.65 g). This extract is treated in the same manner as described in the above (b) to obtain a fraction having a chromatographically single spot. The fraction is concentrated under reduced pressure to give a pale yellow, syrup-like clavulone-3 (255 mg).

The compound obtained above has a molecular formula: $C_{25}H_{34}O_7$ and has a chemical structure of the formula (3) as shown hereinbefore, and shows the following properties:

High mass spectrum: 446.2286 (error: −1.6 mMU);
$[\alpha]_D$ (CHCl$_3$): +45.5° (c=0.22);
UV$\lambda_{max}^{EtOH}$ (nm): 230 ($\epsilon$=17,200), 295 ($\epsilon$=17,600);
IR$\nu_{max}^{film}$ (cm$^{-1}$): 1735, 1690, 1640, 1230;
$^1$H-NMR (270 MHz) (CDCl$_3$, δppm): 0.88 (3H, t, J=6.9 Hz), 2.04 (3H, s), 2.10 (3H, s), 2.39 (2H, t, J=7.5 Hz), 2.66 (1H, dd, J=7, 14.5 Hz), 2.86 (1H, dd, J=7, 14.5 Hz), 3.67 (3H, s), 5.21 (1H, dt, J=11,7 Hz), 5.52 (1H, dt, J=11, 8 Hz), 5.44 (1H, q, J=6 Hz), 6.02 (1H, dd, J=6, 15.5 Hz), 6.36 (1H, d, J=6.3 Hz), 7.74 (1H, dd, J=11.2, 15.5 Hz), 6.52 (1H, d, J=11.2 Hz), 7.50 (1H, d, J=6.3 Hz);
$^{13}$C-NMR (67.8 MHz) (CDCl$_3$, δppm): 14.0 (q), 21.0 (q), 21.7 (q), 22.5 (t), 27.4 (t), 29.1 (t), 29.2 (t), 29.8 (t), 31.5 (t), 35.6 (t), 51.7 (q), 72.5 (d), 85.3 (s), 121.4 (d), 126.5 (d), 133.4 (d), 134.8 (d), 135.7 (s), 136.7 (d), 141.0 (d), 156.1 (d), 169.7 (s), 170.1 (s), 173.1 (s), 194.1 (s).

(e) The fraction (1.1 g) and fraction (0.31 g) containing a few impurities obtained in the above (b) and (c), respectively are combined, and the mixture is subjected to silica gel chromatography (3.5×45 cm), followed by eluting with benzene-ethyl acetate (15:1 by volume) to give clavulone-1 (540 mg) and clavulone-2 (214 mg).

Thus, from the ethyl acetate extract (30 g) obtained in the above (a), there are obtained clavulone-1 (780 mg), clavulone-2 (744 mg) and clavulone-3 (255 mg) in total.

(f) Isolation of clavulone-4:

Fraction-5 (0.86 g) obtained above is passed through a polystyrene gel column (3×40 cm) and eluted with methanol. The resulting crude fraction (240 mg) is further passed through a packed column (Lichroprep RP-8 (40–63 μm), type B, manufactured by Merck & Co.), followed by eluting with 80% methanol to give a pure clavulone-4 (75 mg) as a pale yellow, oily substance.

The compound obtained above has a molecular formula: $C_{27}H_{36}O_9$ and has a chemical structure of the formula (4) as shown hereinbefore and shows the following properties:

Mass (m/z): 504 (M+);
$[\alpha]_D^{20}$: +3.7° (c=0.54, $CHCl_3$);
IR $\nu_{max}^{film}$ ($cm^{-1}$): 1730, 1700, 1640, 1235;
UV$\lambda_{max}^{EtOH}$ (nm): 230 (ε=14,200), 292 (ε=18,700);
$^1$H-NMR (270 MHz) ($CDCl_3$, δppm): 1.33 (4H, m), 1.61 (2H, q, J=6.9 Hz), 2.05 (3H, s), 2.07 (3H, s), 2.08 (3H, s), 2.38 (2H, t, J=7.3 Hz), 2.69 (1H, dd, J=7.6, 16 Hz), 2.87 (1H, dd, J=7.3, 16 Hz), 3.68 (3H, s), 4.04 (2H, t, J=6.9 Hz), 5.20 (1H, m), 5.41 (1H, q, J=7 Hz), 5.51 (1H, dt, J=11, 7.3 Hz), 6.03 (1H, dd, J=7.0, 14.8 Hz), 6.41 (1H, d, J=5.9 Hz), 6.74 (1H, dd, J=12.2, 14.8 Hz), 6.86 (1H, d, J=12.2 Hz), 7.47 (1H, d, J=5.9 Hz);
$^{13}$C-NMR (67.8 MHz) ($CDCl_3$, δppm): 21.2 (q), 21.0 (q, 2C), 25.6 (t), 27.3 (t), 28.5 (t), 29.2 (t, 2C), 29.5 (t), 36.0 (t), 51.8 (q), 64.4 (t), 72.8 (d), 85.0 (s), 121.5 (d), 126.8 (d), 129.3 (d), 134.5 (d), 135.0 (d), 136.8 (s), 141.3 (d), 158.1 (d), 169.5 (s), 169.9 (s), 171.2 (s), 172.9 (s), 193.3 (s).

(g) Isolation of clavulone-5:

Fraction-6 (1.1 g) obtained in the above (a) is passed through a polystyrene gel column (3×45 cm) and eluted with methanol to give a decolored, crude fraction (265 mg). This syrup-like substance is passed through a packed column in the same manner as described in the above (b), followed by eluting with 80% methanol under detecting with a thin layer chromatography to obtain two fractions; Fraction-6a (20 mg) and fraction-6b (125 mg).

The compound on fraction-6b per se is pure clavulone-5 and is a pale yellow oily substance and has a molecular formula: $C_{27}H_{36}O_9$ and has a chemical structure of the formula (5) as shown hereinbefore and shows the following properties:

$[\alpha]_D$: +26.4° (c=0.86, $CHCl_3$);
IR$\nu_{max}^{film}$ ($cm^{-1}$): 1740, 1730, 1695, 1640, 1620, 1235;
UV$\lambda_{max}^{EtOH}$ (nm): 230 (ε=12,400), 295 (ε=12,100);
$^1$N-NMR (270 MHz) ($CDCl_3$, δppm): 2.02 (3H, s), 2.05 (3H,s), 2.10 (3H, s), 2.39 (2H, t, J=7.6 Hz), 2.62 (1H, dd, J=14.2, 7.6 Hz), 2.87 (1H, dd, J=14.2, 7.3 Hz), 3.68 (3H, s), 4.04 (2H, t, J=6.9 Hz), 5.21 (1H, m), 5.44 (1H, q, J=5.9 Hz), 5.51 (1H, m), 6.03 (1H, dd, J=5.9, 15.5 Hz), 6.36 (1H, d, J=6.3 Hz), 6.52 (1H, d, J=11.2 Hz), 7.50 (1H, d, J=6.3 Hz), 7.74 (1H, dd, J=11.2, 15.5 Hz);
C-NMR (67.8 MHz) ($CDCl_3$, δppm): 21.0 (q, 2C), 21.7 (q), 25.6 (t), 27.3 (t), 28.5 (t), 29.0 (t), 29.2 (t), 29.8 (t), 35.6 (t), 51.7 (q), 64.4 (t), 72.5 (d), 85.2 (s), 121.8 (d), 126.4 (d), 133.5 (d), 134.2 (d), 135.6 (s), 136.9 (d), 141.1 (d), 156.0 (d), 169.9 (s), 170.1 (s), 171.2 (s), 173.1 (s), 194.0 (s).

(h) Isolation of clavulone-6:

Fraction-6a (20 mg) obtained in the above (g) is again passed through a packed column and eluted with 80% methanol to give clavulone-6 (15 mg) as a pale yellow oily substance.

This compound has a molecular formula: $C_{27}H_{36}O_9$ and has a chemical structure of the formula (6) as shown hereinbefore and shows the following properties:

$[\alpha]_D$: −31.1° (c=0.09, $CHCl_3$);
IR$\nu_{max}^{film}$ ($cm^{-1}$): 1735, 1705, 1640, 1235;
UV$\lambda_{max}^{EtOH}$ (nm): 230, 292;
$^1$H-NMR (270 MHz) ($CDCl_3$, δppm): 2.03 (3H, s), 2.05 (6H, s), 2.38 (2H, t, J=7.5 Hz), 2.66 (1H, dd, J=8, 14.5 Hz), 3.00 (1H, dd, J=7, 14.5 Hz), 3.70 (3H, s), 4.04 (2H, t, J=6.6 Hz), 5.22 (1H, m), 5.47 (1H, m), 5.79 (1H, m), 5.84 (1H, t, J=10.2 Hz), 6.42 (1H, d, J=6.3 Hz), 6.58 (1H, dd, J=10.2, 12.5 Hz), 7.27 (1H, d, J=12.5 Hz), 7.47 (1H, d, J=6.3 Hz).

EXAMPLE 2

Clavulone-1 (100 mg) is dissolved in methanol (5 ml) and thereto is added sodium borohydride (50 mg), and the mixture is stirred at room temperature for 30 minutes. To the reaction mixture is added acetone (0.5 ml) in order to decompose excess reducing agent. After adding a saturated aqueous saline solution (50 ml), the mixture is extracted with ethyl acetate (50 ml). The ethyl acetate solution is washed three times with a saturated aqueous saline solution, dried over anhydrous sodium sulfate and then the solvent is evaporated under reduced pressure to give a colorless oily substance (110 mg). This oily substance is subjected to a low pressure liquid chromatography (n-hexane-ethyl acetate=1:1 by volume) with a silica gel column (Merck Lobar column) to give clavulone-7 (40 mg, yield: 40%) as a colorless oily substance.

The compound obtained above has a molecular formula: $C_{25}H_{38}O_7$ and has a chemical structure of the formula (7) as shown hereinbefore and shows the following properties:

$[\alpha]_D$ ($CHCl_3$): −109.5°;
UV$\lambda_{max}^{EtOH}$ (nm): 248 (ε=24,700).

EXAMPLE 3

In the same manner as described in Example 2, clavulone-2 is reduced with sodium borohydride to give clavulone-9 (yield: 36%).

This compound has a molecular formula: $C_{25}H_{38}O_7$ and has a chemical structure of the formula (9) as shown hereinbefore. $[\alpha]_D$ ($CHCl_3$): −24.25°.

EXAMPLE 4

In the same manner as described in Example 2, clavulone-3 is reduced with sodium borohydride to give clavulone-10 (yield: 36%).

This compound has a molecular formula: $C_{25}H_{38}O_7$ and has a chemical structure of the formula (10) as shown hereinbefore. $[\alpha]_D$ ($CHCl_3$): −5.8°.

EXAMPLE 5

Clavulone-7 (49 mg) obtained in the above Example 2 is dissolved in carbon tetrachloride (2 ml) and thereto are added acetic anhydride (0.2 ml), triethylamine (0.5 ml) and dimethylaminopyridine (10 mg) in this order, and the mixture is stirred at room temperature for 21 hours. After adding thereof ethyl acetate (50 ml), the mixture is washed with water, a saturated aqueous copper sulfate solution, water and a saturated aqueous saline solution in this order, and then dried. The solvent is evaporated under reduced pressure to give a brown oily substance (64 mg). This substance is subjected to a low pressure liquid chromatography (n-hexane-ethyl acetate=2:1 by volume) with a silica gel column (Merck Lobar column) to give clavulone-8 (40 mg, yield: 75%) as a pale yellow oily substance.

This compound has a molecular formula: $C_{27}H_{40}O_8$ and has a chemical structure of the formula (8) as shown hereinbefore. $UV\lambda_{max}^{EtOH}$ (nm): 247 ($\epsilon$=27,000).

EXAMPLE 6

Clavulone-7 (15 mg) obtained in the above Example 2 is dissolved in methylene chloride (2 ml), and thereto is added pyridinium chlorochromate (60 mg), and the mixture is vigorously stirred at room temperature for 4 hours. The reaction mixture is passed through a silica gel column, followed by washing with methylene chloride. The solution passed through the column and the washing liquid are combined, and the solvent is evaporated under reduced pressure to give a greenish brown oily substance. This substance is purified by a low pressure liquid chromatography (n-hexane-ethyl acetate=1:1 by volume) with a silica gel column (Merck Lobar column) to give clavulone-11 (yield: 95%) as a colorless oily substance.

This compound has a molecular formula: $C_{25}H_{36}O_7$ and has a chemical structure of the formula (11) as shown hereinbefore and shows the following properties:

High mass spectrum: 388.2230 (M-AcOH) (error: −1.7 mMU);
$[\alpha]_D$ (CHCl$_3$): −68.2°;
$UV\lambda_{max}^{EtOH}$ (nm): 287 ($\epsilon$=21,500).

EXAMPLE 7

Clavulone-1 (100 mg) is dissolved in ethanol (10 ml) and thereto is added 5% palladium-carbon (30 mg), and the mixture is vigorously stirred under hydrogen gas at room temperature for 30 minutes. The reaction mixture is filtered to remove the catalyst. The filtrate is evaporated under reduced pressure to remove the solvent to give a colorless oily substance (69 mg). This oily substance is separated by a low pressure liquid chromatography (n-hexane-ethyl acetate=1:1 by volume) with a silica gel column (Merck Lobar column) to give colorless oily clavulone-13 (12 mg, yield: 14%) and colorless oily clavulone-12 (36 mg, yield: 41%).

This clavulone-12 obtained above has a molecular formula: $C_{23}H_{38}O_5$ and has a chemical structure of the formula (12) as shown hereinbefore and shows the following properties:

High mass spectrum: 394.2706 (error: −1.0 mMU);
$[\alpha]_D$ (CHCl$_3$): +7.0°;
$UV\lambda_{max}^{EtOH}$ (nm): 235 ($\epsilon$=14,200).

Clavulone-13 obtained above has a molecular formula: $C_{23}H_{40}O_5$ and has a chemical structure of the formula (13) as shown hereinbefore and shows high mass spectrum: 396.2899 (error: 2.5 mMU).

The above procedure is repeated except that clavulone-2 or clavulone-3 is used instead of clavulone-1, there are clavulone-12 and clavulone-13 in the almost same yield.

| Preparation 1 | |
|---|---|
| Component | Part by weight |
| Clavulone-2 | 1 |
| Tween 80 | 0.1 |
| Mannitol | 5 |
| Purified water | 94 |

The above components are mixed well with stirring, filtered with a membrane filter and then lyophilized to give a powder for injection.

| Preparation 2 | |
|---|---|
| Component | Part by weight |
| Clavulone-1 | 0.2 |
| A nonionic surfactant | 2 |
| Distilled water for injection | 98 |

The above components are mixed well and sterilized to give a liquid for injection.

| Preparation 3 | |
|---|---|
| Component | Part by weight |
| Clavulone-2 | 3 |
| Gelatine | 1 |
| Distilled water for injection | 96 |

The above components are mixed well and sterilized to give a liquid for injection.

| Preparation 4 | |
|---|---|
| Component | Part by weight |
| Clavulone-1 | 5 |
| Light silica | 5 |
| Avicel (microcrystalline cellulose) | 20 |
| Lactose | 70 |

The above components are mixed well to give a powder suitable for oral administration.

| Preparation 5 | |
|---|---|
| Component | Part by weight |
| Clavulone-3 | 1 |
| Panasate 800 | 99 |

Clavulone-3 is dissolved in panasate 800 and the resulting solution is packed within soft capsules.

What is claimed is:

1. A substantially pure clavulone derivative of the formula:

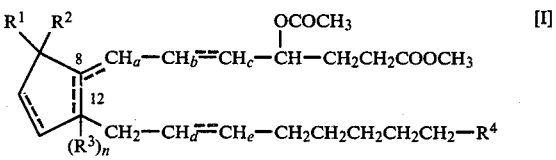

wherein $R^1$ and $R^2$ combine together to form a keto group or either one of $R^1$ and $R^2$ is hydrogen atom and another one of them is hydroxy or acetoxy group, $R^3$ and $R^4$ are the same or different and are each hydrogen atom or acetoxy group, n is 0 or 1, provided that when the C—C bond between 8 and 12 positions is double bond, n is 0, a, b, c, d and e are each an integer of 1 or 2, and the dotted line means that the C—C bond is a single bond or double bond, or a salt thereof.

2. The clavulone derivative according to claim 1, which is a compound of the formula:

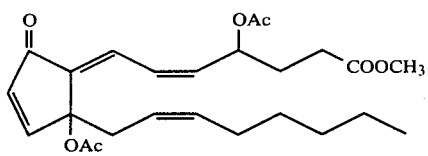

wherein Ac means acetyl group.

3. The clavulone derivative according to claim 1, which is a compound of the formula:

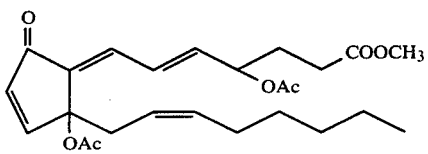

wherein Ac means acetyl group.

4. The clavulone derivative according to claim 1, which is a compound of the formula:

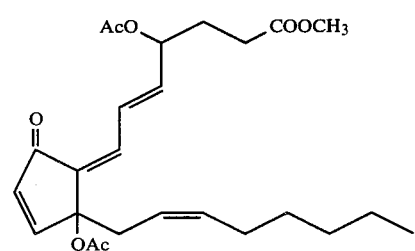

wherein Ac means acetyl group.

5. The clavulone derivative according to claim 1, which is a compound of the formula:

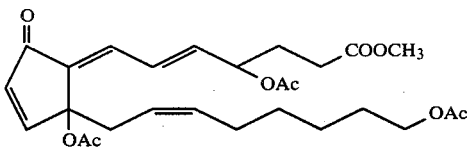

wherein Ac means acetyl group.

6. The clavulone derivative according to claim 1, which is a compound of the formula:

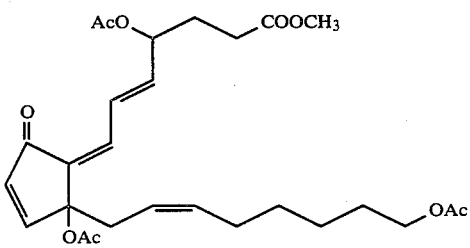

wherein Ac means acetyl group.

7. The clavulone derivative according to claim 1, which is a compound of the formula:

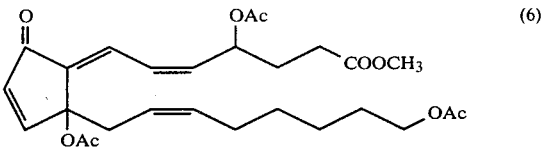

wherein Ac means acetyl group.

8. The clavulone derivative according to claim 1, which is a compound of the formula:

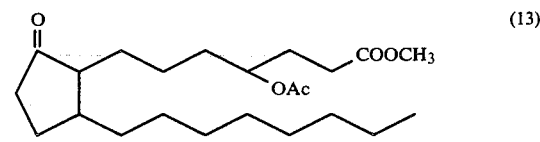

wherein Ac means acetyl group.

9. A pharmaceutical anti-inflammatory composition comprising:

(a) an effective amount of a clavulone of the formula:

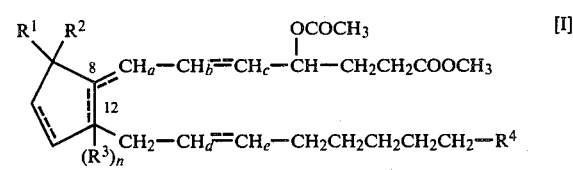

wherein
$R^1$ and $R^2$ combined together form a keto group, or either one of $R^1$ and $R^2$ is hydrogen and another one of them is hydroxy or acetoxy,
$R^3$ and $R^4$ are the same or different and each is hydrogen or acetoxy,
n is 0 or 1, provided that when the C—C bond between the 8 and 12 positions is a double bond, n is 0,
a, b, c, d and e are 1 or 2, and
the dotted line means that the C—C bond is a single bond or double bond, or a salt thereof; and (b) a pharmaceutically acceptable carrier or diluent.

10. A method of reducing or preventing inflammation comprising administering to a subject in need of such treatment an anti-inflammatory effective amount of a clavulone of the formula:

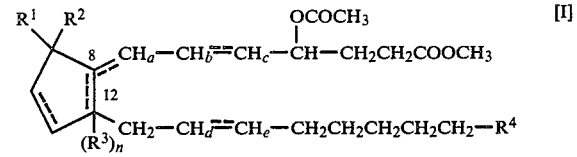

wherein
$R^1$ and $R^2$ combined together form a keto group, or either one of $R^1$ and $R^2$ is hydrogen and another one of them is hydroxy or acetoxy,
$R^3$ and $R^4$ are the same or different and each is hydrogen or acetoxy,
n is 0 or 1, provided that when the C—C bond between the 8 and 12 positions is a double bond, n is 0,
a, b, c, d and e are 1 or 2, and the dotted line means that the C—C bond is a single bond or double bond, or a salt thereof.

11. A method of reducing the proliferation of tumorgenic cells selected from the group consisting of leukemia cells, fibrosarcoma cells, carcinoma cells and melanoma cells comprising administering to a subject in need of such treatment an anti-tumorgenic effective amount of a clavulone of the formula:

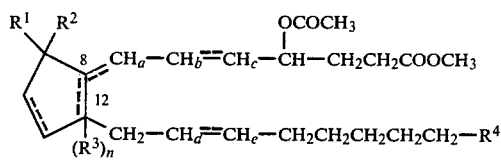

wherein $R^1$ and $R^2$ combined together from a keto group, or either one of $R^1$ and $R^2$ is hydrogen and another one of them is hydroxy or acetoxy;

$R^3$ and $R^4$ are the same or different and each is hydrogen or acetoxy;

n is 0 or 1, provided that when the C—C bond between the 8 and 12 positions is a double bond, n is 0, a, b, c, d and e are each 1 or 2, and the dotted line means that the C—C bond is a single bond or double bond, or a salt thereof.

12. The method of claim 11 wherein the cells are leukemia cells.

13. The method of claim 11 wherein the cells are fibrosarcoma cells.

14. The method of claim 11 wherein the cells are carcinoma cells.

15. The method of claim 11 wherein the cells are melanoma cells.